(12) United States Patent
Riley et al.

(10) Patent No.: US 8,844,073 B2
(45) Date of Patent: Sep. 30, 2014

(54) APPARATUS FOR SUPPORTING AND MONITORING A PERSON

(75) Inventors: Carl W. Riley, Milan, IN (US); Dan R. Tallent, Hope, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 553 days.

(21) Appl. No.: 13/153,592

(22) Filed: Jun. 6, 2011

(65) Prior Publication Data

US 2011/0301440 A1 Dec. 8, 2011

Related U.S. Application Data

(60) Provisional application No. 61/352,033, filed on Jun. 7, 2010.

(51) Int. Cl.
| | |
|---|---|
| *A61G 7/05* | (2006.01) |
| *A61G 7/018* | (2006.01) |
| *A61B 5/0205* | (2006.01) |
| *A61B 5/00* | (2006.01) |
| *G06F 19/00* | (2011.01) |
| *A61B 5/021* | (2006.01) |
| *A61B 5/024* | (2006.01) |
| *A61B 5/08* | (2006.01) |
| *A61B 5/11* | (2006.01) |
| *A61B 5/1455* | (2006.01) |

(52) U.S. Cl.
CPC ............ *A61G 7/018* (2013.01); *A61B 5/02055* (2013.01); *A61B 5/021* (2013.01); *A61B 5/024* (2013.01); *A61B 5/0816* (2013.01); *A61B 5/1113* (2013.01); *A61B 5/14551* (2013.01); *A61B 5/411* (2013.01); *A61B 5/6891* (2013.01); *A61B 5/7275* (2013.01); *A61B 2562/0247* (2013.01); *G06F 19/3406* (2013.01); *G06F 19/3418* (2013.01); *G06F 19/3431* (2013.01)
USPC ............. 5/424; 5/600; 5/616; 177/144

(58) Field of Classification Search
USPC ................ 5/600, 616, 424; 177/144
See application file for complete search history.

(56) References Cited

U.S. PATENT DOCUMENTS

| | | | |
|---|---|---|---|
| 2,194,809 | A | 3/1940 | Powell, Jr. |
| 3,325,799 | A | 6/1967 | Farris |

(Continued)

FOREIGN PATENT DOCUMENTS

| | | |
|---|---|---|
| EP | 2 281 540 A2 | 9/2011 |
| EP | 2 417 908 A1 | 2/2012 |

(Continued)

OTHER PUBLICATIONS

L. Tarassenko et al., "Biosign™: Multi-Parameter Monitoring for Early Warning of Patient Deterioration", (6 pages).

(Continued)

*Primary Examiner* — Michael Trettel
(74) *Attorney, Agent, or Firm* — Barnes & Thornburg LLP

(57) ABSTRACT

A person-support structure includes a control system, an input configured to communicate a first input signal to the control system, and a sensor configured to sense a physiological characteristic of a person supported on the person-support structure. The sensor communicates a second input signal corresponding to the physiological characteristic to the control system. The control system calculates a condition score as a function of the first input signal and the physiological characteristic of the person and compares the condition score to a predetermined threshold. The control system scales at least one of the physiological characteristic of the person and the predetermined threshold as a function of the first input signal.

20 Claims, 7 Drawing Sheets

(56) References Cited

U.S. PATENT DOCUMENTS

| | | | |
|---|---|---|---|
| 3,631,438 A | 12/1971 | Lewin | |
| 3,644,950 A | 2/1972 | Lindsay, Jr. | |
| 3,727,606 A | 4/1973 | Sielaff | |
| 3,836,900 A | 9/1974 | Mansfield | |
| 3,996,928 A | 12/1976 | Marx | |
| 4,146,885 A | 3/1979 | Lawson, Jr. | |
| 4,195,287 A | 3/1980 | McCoy et al. | |
| 4,245,651 A | 1/1981 | Frost | |
| 4,422,458 A | 12/1983 | Kravath | |
| 4,481,686 A | 11/1984 | Lacoste | |
| 4,483,029 A | 11/1984 | Paul | |
| 4,485,505 A | 12/1984 | Paul | |
| 4,525,885 A | 7/1985 | Hunt et al. | |
| 4,559,656 A | 12/1985 | Foster | |
| 4,564,965 A | 1/1986 | Goodwin | |
| 4,595,023 A | 6/1986 | Bonnet | |
| 4,602,643 A | 7/1986 | Dietz | |
| 4,637,083 A | 1/1987 | Goodwin | |
| 4,657,026 A | 4/1987 | Tagg | |
| 4,677,857 A | 7/1987 | Feldmann | |
| 4,681,098 A | 7/1987 | Lee | |
| 4,694,520 A | 9/1987 | Paul et al. | |
| 4,757,825 A | 7/1988 | Diamond | |
| 4,799,276 A | 1/1989 | Kadish | |
| 4,838,309 A | 6/1989 | Goodwin | |
| 4,889,131 A | 12/1989 | Salem et al. | |
| 4,934,468 A | 6/1990 | Koerber, Sr. et al. | |
| 4,935,968 A | 6/1990 | Hunt et al. | |
| 4,942,635 A | 7/1990 | Hargest et al. | |
| 4,949,412 A | 8/1990 | Goode | |
| 4,949,414 A | 8/1990 | Thomas et al. | |
| 4,967,195 A | 10/1990 | Shipley | |
| 4,971,065 A | 11/1990 | Pearce | |
| 5,010,772 A | 4/1991 | Bourland et al. | |
| 5,052,067 A | 10/1991 | Thomas et al. | |
| 5,057,819 A | 10/1991 | Valenti | |
| 5,060,174 A | 10/1991 | Gross | |
| 5,101,828 A | 4/1992 | Welkowitz et al. | |
| 5,117,518 A | 6/1992 | Schild | |
| 5,170,364 A | 12/1992 | Gross et al. | |
| 5,182,826 A | 2/1993 | Thomas et al. | |
| 5,184,112 A | 2/1993 | Gusakov | |
| 5,276,432 A | 1/1994 | Travis | |
| 5,283,735 A | 2/1994 | Gross et al. | |
| 5,539,942 A | 7/1996 | Melou | |
| 5,561,412 A | 10/1996 | Novak et al. | |
| 5,664,270 A | 9/1997 | Bell et al. | |
| 5,738,102 A | 4/1998 | Lemelson | |
| 5,794,288 A | 8/1998 | Soltani et al. | |
| 5,815,864 A | 10/1998 | Sloop | |
| 5,817,146 A | 10/1998 | Augustine | |
| 5,829,081 A | 11/1998 | Pearce | |
| 5,873,137 A | 2/1999 | Yavets-Chen | |
| 5,934,280 A | 8/1999 | Viard et al. | |
| 5,964,720 A | 10/1999 | Pelz | |
| 5,970,789 A | 10/1999 | Meyer et al. | |
| 6,009,580 A | 1/2000 | Caminade et al. | |
| 6,011,477 A | 1/2000 | Teodorescu et al. | |
| 6,034,526 A | 3/2000 | Montant et al. | |
| 6,067,019 A | 5/2000 | Scott | |
| 6,067,466 A | 5/2000 | Selker et al. | |
| 6,079,068 A | 6/2000 | Viard | |
| 6,094,762 A | 8/2000 | Viard et al. | |
| 6,208,250 B1 | 3/2001 | Dixon et al. | |
| 6,212,718 B1 | 4/2001 | Stolpmann et al. | |
| 6,493,568 B1 | 12/2002 | Bell et al. | |
| 6,721,980 B1 | 4/2004 | Price et al. | |
| 6,984,207 B1 | 1/2006 | Sullivan et al. | |
| 7,031,857 B2 | 4/2006 | Tarassenko et al. | |
| 7,077,810 B2 | 7/2006 | Lange et al. | |
| 7,127,948 B2 | 10/2006 | Tavares et al. | |
| 7,183,930 B2 | 2/2007 | Basir et al. | |
| 7,242,306 B2 | 7/2007 | Wildman et al. | |
| 7,242,308 B2 | 7/2007 | Ulrich et al. | |
| 7,245,956 B2 | 7/2007 | Matthews et al. | |
| 7,248,933 B2 | 7/2007 | Wildman | |
| 7,253,366 B2 | 8/2007 | Bhai | |
| 7,289,844 B2 | 10/2007 | Misczynski et al. | |
| 7,296,312 B2 | 11/2007 | Menkedick et al. | |
| 7,304,580 B2 | 12/2007 | Sullivan et al. | |
| 7,306,564 B2 | 12/2007 | Nakatani et al. | |
| 7,314,451 B2 | 1/2008 | Halperin et al. | |
| 7,315,535 B2 | 1/2008 | Schuman | |
| 7,319,386 B2 | 1/2008 | Collins, Jr. et al. | |
| 7,330,127 B2 | 2/2008 | Price et al. | |
| 7,443,303 B2 | 10/2008 | Spear et al. | |
| 7,515,059 B2 | 4/2009 | Price et al. | |
| 7,629,890 B2 | 12/2009 | Sullivan et al. | |
| 7,834,770 B2 * | 11/2010 | Kazuno | 340/573.4 |
| 8,381,336 B2 * | 2/2013 | Kazuno et al. | 5/600 |
| 8,413,273 B2 * | 4/2013 | Hornbach et al. | 5/611 |
| 2001/0004778 A1 | 6/2001 | Heimbrock et al. | |
| 2003/0144829 A1 | 7/2003 | Geatz et al. | |
| 2004/0111045 A1 | 6/2004 | Sullivan et al. | |
| 2005/0027416 A1 | 2/2005 | Basir et al. | |
| 2005/0168341 A1 | 8/2005 | Reeder et al. | |
| 2005/0190062 A1 | 9/2005 | Sullivan et al. | |
| 2005/0190068 A1 | 9/2005 | Gentry et al. | |
| 2006/0101581 A1 | 5/2006 | Blanchard et al. | |
| 2006/0179952 A1 | 8/2006 | Tavares et al. | |
| 2007/0056101 A1 | 3/2007 | Mahajan et al. | |
| 2007/0118054 A1 | 5/2007 | Pinhas et al. | |
| 2007/0210917 A1 | 9/2007 | Collins, Jr. et al. | |
| 2007/0247316 A1 | 10/2007 | Wildman et al. | |
| 2008/0060138 A1 | 3/2008 | Price et al. | |
| 2008/0094207 A1 | 4/2008 | Collins, Jr. et al. | |
| 2008/0095156 A1 | 4/2008 | Schuman | |
| 2008/0114260 A1 | 5/2008 | Lange et al. | |
| 2008/0146892 A1 | 6/2008 | LeBoeuf et al. | |
| 2008/0269625 A1 | 10/2008 | Halperin et al. | |
| 2008/0275349 A1 | 11/2008 | Halperin et al. | |
| 2008/0281170 A1 | 11/2008 | Eshelman et al. | |
| 2009/0044334 A1 * | 2/2009 | Parsell et al. | 5/424 |
| 2009/0054735 A1 | 2/2009 | Higgins et al. | |
| 2009/0069642 A1 | 3/2009 | Gao et al. | |
| 2009/0070939 A1 | 3/2009 | Hann | |
| 2009/0088606 A1 | 4/2009 | Cuddihy et al. | |
| 2009/0093686 A1 | 4/2009 | Hu et al. | |
| 2009/0163774 A1 | 6/2009 | Thatha et al. | |
| 2009/0216556 A1 | 8/2009 | Martin et al. | |
| 2009/0260158 A1 * | 10/2009 | Kazuno et al. | 5/600 |
| 2009/0326339 A1 | 12/2009 | Horvitz | |
| 2010/0099954 A1 | 4/2010 | Dickinson et al. | |
| 2010/0101022 A1 | 4/2010 | Riley et al. | |

FOREIGN PATENT DOCUMENTS

| | | |
|---|---|---|
| JP | 06315424 A2 | 11/1994 |
| WO | 98/34577 A1 | 8/1998 |
| WO | 2007/016054 A2 | 2/2007 |
| WO | 2009/108228 A1 | 9/2009 |

OTHER PUBLICATIONS

C. P. Subbe, et al., "Validation of a modified Early Warning Score in medical admissions", *Q J Med* 2001: 94:521-526.

Marilyn Hravnak et al., "Defining the Incidence of Cardiorespiratory Instability in Patients in Step-down Units Using an Electronic Integrated Monitoring System", *Arch Intern Med*, vol. 168 (No. 12), Jun. 23, 2008, 1300-1308.

L. Tarassenko, et al., "Integrated monitoring and analysis for early warning of patient deterioration", *British Journal of Anasthesia*, May 17, 2006, (5 pages).

"Visensia", *OBS Medical Ltd.* (4 pages).

Coba V. Rubinfeld I, et al., "Can the Visensia Index Score Predict Mortality in High Risk Injured Patients?", (1 page).

European search report from related EP 11 16 8897 dated Sep. 22, 2011, 7 pages.

* cited by examiner

APPARATUS FOR SUPPORTING AND MONITORING A PERSON

CROSS-REFERENCE TO RELATED APPLICATIONS

The present application claims the benefit, under 35 U.S.C. §119(e), of U.S. Provisional Application No. 61/352,033 which was filed Jun. 7, 2010 and which is hereby incorporated by reference herein.

The present application relates to U.S. application Ser. No. 13/153,672, filed concurrently herewith and titled "Apparatus for Supporting and Monitoring a Person".

BACKGROUND

This disclosure relates to person support apparatuses. More particularly, but not exclusively, the present disclosure relates to person support apparatuses that incorporate or are used with vital signs monitoring devices and movement detection systems, and prediction of the onset of a condition.

Person support apparatuses can include beds, chairs, stretchers, seats, mattresses, therapy surfaces, furniture, and the like, or other apparatuses that support a person. Hospital beds and stretchers, hospital mattresses, and wheelchairs are examples of such apparatuses that support persons. Consumer beds, chairs, and furniture are also examples of such person support apparatuses, as are seats for vehicles, businesses, and venues.

Vital signs monitors monitor one or more physiological parameters of a person, such as body temperature, pulse rate, heart rate, blood pressure, and respiratory rate, as well as other body signs, such as end-tidal $CO_2$, $SpO_2$ (saturation of oxygen in arterial blood flow, sometimes referred to as pulse oximetry), and other indicators of the person's physiological state. Movement and/or position detection systems monitor the movement of a person to determine if they are attempting to exit the support apparatus. Movement and/or position detection systems are sometimes included as part of a hospital bed.

While various systems have been developed, there is still a need for further contributions and improvements in these areas of technology, particularly with regard to predicting the onset of an adverse condition prior to the occurrence of the condition.

SUMMARY

The present disclosure includes one or more of the features recited in the appended claims and/or the following features which alone or in any combination may comprise patentable subject matter.

A method of predicting the onset of an adverse condition, according to the disclosure, may include receiving an input from a user interface, receiving information corresponding to a physiological characteristic of a person supported on the person-support apparatus, calculating a condition score as a function of the physiological characteristic of a person and the status of the input from the user interface, and alerting a caregiver if the condition score is greater than a predetermined threshold, wherein at least one of the physiological characteristic and the predetermined threshold is scaled as a function of the input. The physiological characteristic may be scaled as a function of the input from the user interface. The predetermined threshold may be scaled as a function of the input from the user interface.

Also according to the disclosure, a method of predicting the onset of an adverse condition may include receiving information corresponding to the status of a person-support apparatus, receiving information corresponding to a physiological characteristic of a person supported on the person-support apparatus, calculating a condition score as a function of the physiological characteristic of a person and the status of the person-support apparatus, and alerting a caregiver if the condition score is greater than a predetermined threshold, wherein at least one of the physiological characteristic and the predetermined threshold is scaled as a function of the status of the person-support apparatus. The physiological characteristic may be scaled as a function of the status of the person-support apparatus. The predetermined threshold may be scaled as a function of the status of the person-support apparatus. The status of the person-support apparatus may include at least one of a height of an upper frame, an angle at which a section of a deck movably coupled to an upper frame is with respect to the upper frame, a position of a siderail, at least one of a Trendelenburg position and reverse Trendelenburg position, a CPR function status, a center of gravity of the person-support apparatus, a position of a person on the person-support apparatus, and a status of a person-support apparatus alarm.

Another method of predicting the onset of an adverse condition, according to the disclosure, may include receiving information corresponding to the history of a person, receiving information corresponding to a physiological characteristic of a person, calculating a condition score as a function of the physiological characteristic of the person and the history of the person, and alerting a caregiver if the condition score is greater than a predetermined threshold, wherein at least one of the physiological characteristic and the predetermined threshold is scaled as a function of the history of the person. The physiological characteristic may be scaled as a function of the history of the person. The predetermined threshold may be scaled as a function of the history of the person. The history of the person may include at least one of a preference of a person, a tendency of a person, an electronic medical record (EMR) of a person, a pressure ulcer risk assessment of a person, a medical history of a person, an allergy of a person, a medical condition of a person, a diagnosis of a person, a medication chart for a person, a caregiver assignment history for a person, and a habit of a person.

Also according to the disclosure, a method of predicting the onset of an adverse condition may include receiving information corresponding to a characteristic of a care facility, receiving information corresponding to a physiological characteristic of a person in the care facility, calculating a condition score as a function of the physiological characteristic of the person and the characteristic of the care facility, and alerting a caregiver if the condition score is greater than a predetermined threshold, wherein at least one of the physiological characteristic and the predetermined threshold is scaled as a function of the characteristic of the care facility. The physiological characteristic may be scaled as a function of the characteristic of the care facility. The predetermined threshold may be scaled as a function of the characteristic of the care facility. The characteristic of the care facility may include at least one of a staffing level of the care facility, at least one of a date and a time of day, an amount of people in the care facility, a size of the care facility, a location of a caregiver within the care facility, a progress of a caregiver on their rounds, and an acuity of people in the care facility.

Yet another method of predicting the onset of an adverse condition, according to the disclosure, may include receiving information corresponding to the status of a person-support surface, receiving information corresponding to a physiological characteristic of a person supported on the person-support surface, calculating a condition score as a function of the physiological characteristic of the person and the status of the person-support surface, and alerting a caregiver if the condition score is greater than a predetermined threshold, wherein at least one of the physiological characteristic and the predetermined threshold is scaled as a function of the person-support surface. The physiological characteristic may be scaled as a function of the status of the person-support surface. The predetermined threshold may be scaled as a function of the status of the person-support surface. The status of the person-support surface may include at least one of a pressure in a fluid bladder within the person-support surface, a status of a surface therapy, a status of a low-air loss therapy, a status of a percussion vibration therapy, a status of a lateral rotation therapy, a status of an alternating pressure therapy, a status of a surface zone, a status of a surface function, a status of a surface length extension function, a status of a surface length reduction function, a status of a surface width extension function, a status of a surface width reduction function, a status of a turn assist function, a position of a person on the person-support surface, and a morphology of a person on the person-support surface. The sensitivity of the condition score to a particular physiological characteristic may be changed as a function of at least one of a status of a person-support apparatus, a status of a person-support surface, a history of a person, an input from a user input, and a status of a care facility.

Some embodiments may include a control system for a person support system configured to receive input signals from at least one of a sensor and an electronic medical record (EMR), generate a condition score as a function of the input that can corresponding to the likelihood of an adverse condition occurring, and alert a caregiver when the condition score exceeds a predetermined threshold.

According to this disclosure, a person-support structure may comprise a control system, an input configured to communicate a first input signal to the control system, and a sensor configured to sense a physiological characteristic of a person supported on the person-support structure. The sensor may communicate a second input signal corresponding to the physiological characteristic to the control system. The control system may calculate a condition score as a function of the first input signal and the physiological characteristic of the person and may compare the condition score to a predetermined threshold. The control system may further cause an alert signal to be output when the condition score is greater than the predetermined threshold. The control system may scale at least one of the physiological characteristic of the person and the predetermined threshold as a function of the first input signal.

In some embodiments, the input may include a user interface configured to receive a user input, the first input signal including the user input. The person-support structure may include a person-support surface and the input may include a second sensor that may be coupled to the person-support surface and that may be configured to sense a status of the person-support surface such that the first input signal may include a person-support surface status information.

The status of the person-support surface may include at least one of a pressure in a fluid bladder of the person-support surface, a status of a surface therapy, a status of a low-air loss therapy, a status of a percussion vibration therapy, a status of a lateral rotation therapy, a status of an alternating pressure therapy, a status of a surface zone, a status of a surface function, a status of a surface length extension function, a status of a surface length reduction function, a status of a surface width extension function, a status of a surface width reduction function, a status of a turn assist function, a position of a person on the person-support surface, and a morphology of a person on the person-support surface.

Alternatively or additionally, the first input signal may include information corresponding to a characteristic of a care facility. The characteristic of the care facility may include, for example, at least one of a staffing level of the care facility, at least one of a date and a time of day, an amount of people in the care facility, a size of the care facility, a location of a caregiver within the care facility, a progress of a caregiver on their rounds, and an acuity of people in the care facility.

Further alternatively or additionally, the first input signal may include information corresponding to the history of a person. The history of the person may include, for example, at least one of a preference of a person, a tendency of a person, an electronic medical record (EMR) of a person, a pressure ulcer risk assessment of a person, a medical history of a person, an allergy of a person, a medical condition of a person, a diagnosis of a person, a medication chart for a person, a caregiver assignment history for a person, and a habit of a person.

According to this disclosure, the person-support structure may include a bed frame having an upper frame movably supported above a lower frame. The input may include a second sensor that is coupled to the bed frame and that is configured to sense a status of the bed frame. The first input signal may include information corresponding to the status of the bed frame. The status of the bed frame may include, for example, at least one of a height of the upper frame, an angle at which a section of a deck movably coupled to the upper frame is with respect to the upper frame, a position of a siderail, at least one of a Trendelenburg position and reverse Trendelenburg position, a CPR function status, a center of gravity of a person on the bed frame, a position of the person on the bed frame, and a status of a person-support alarm.

According to this disclosure, a method of predicting the onset of an adverse condition is provided. The method may include receiving a first input signal from an input, receiving a second input signal corresponding to a physiological characteristic of a person supported on a person-support structure, calculating a condition score as a function of the first input signal on the physiological characteristic, and alerting a caregiver if the condition score is greater than a predetermined threshold. At least one of the physiological characteristic and the predetermined threshold may be scaled as a function of the first input signal.

In some embodiments, the first input signal may correspond to at least one of a user input, person-support surface status information, a care facility characteristic, a history of a person, and the status of a bed frame. The first input signal may include at least one of a fall risk assessment score and a pressure ulcer risk assessment score. The method may further include configuring a person-support system as a function of the condition score. The person-support system may include at least one of a bed frame and a person-support surface, for example. The method may also further include controlling a fluid supply to a person-support surface as a function of the condition score.

According to this disclosure, the first input signal may include information corresponding to a characteristic of a care facility. The characteristic of the care facility may include, for example, at least one of a staffing level of the care facility, at least one of a date and a time of day, an amount of people in the care facility, a size of the care facility, a location of a caregiver within the care facility, a progress of a caregiver on their rounds, and an acuity of people in the care facility.

Alternatively or additionally, the first input signal may include information corresponding to the history of a person. The history of the person may include, for example, at least one of a preference of a person, a tendency of a person, an electronic medical record (EMR) of a person, a pressure ulcer risk assessment of a person, a medical history of a person, an allergy of a person, a medical condition of a person, a diagnosis of a person, a medication chart for a person, a caregiver assignment history for a person, and a habit of a person.

Additional features, which alone or in combination with any other feature(s), such as those listed above and/or those listed in the claims, can comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

Referring now to the illustrative examples in the drawings, wherein like numerals represent the same or similar elements throughout.

DETAILED DESCRIPTION

Figure 1:
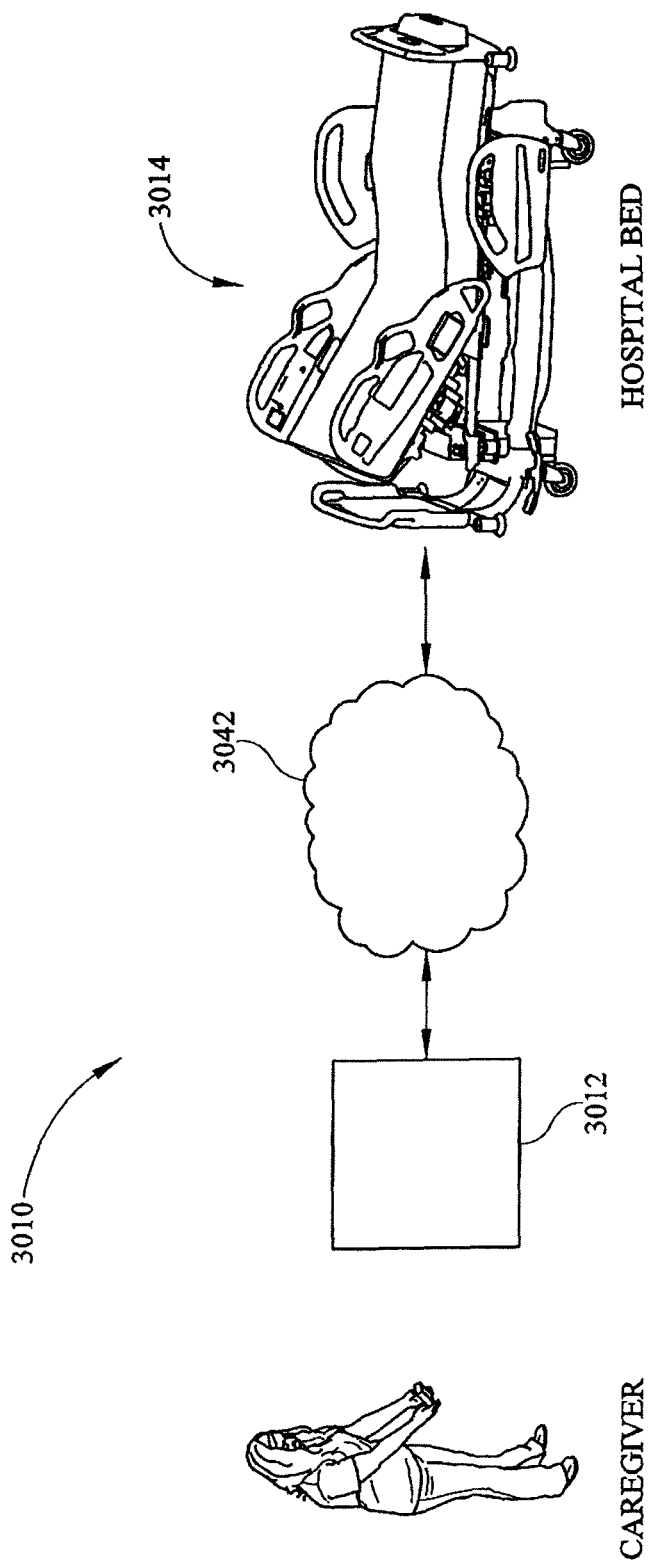
FIG. 1 is a diagrammatic view of person monitoring system according to one or more principles of the present disclosure.

While the present disclosure can take many different forms, for the purpose of promoting an understanding of the principles of the disclosure, reference will now be made to the embodiments illustrated in the drawings, and specific language will be used to describe the same. No limitation of the scope of the disclosure is thereby intended. Various alterations, further modifications of the described embodiments, and any further applications of the principles of the disclosure, as described herein, are contemplated.

One illustrative embodiment includes a control system coupled to a person support system configured to receive input signals corresponding to at least one of bed status information, person position, electronic medical record information, and physiological information, generate a condition score corresponding to the likelihood of an adverse condition occurring, and alert a caregiver when the condition score exceeds a predetermined threshold.

A person monitor system 3010 according to one illustrative embodiment of the current disclosure is shown in FIG. 1. The person monitor system 3010 includes a signaling and communication system 3012 in communication with a person support apparatus 3014. The person monitor system 3010 is configured to provide caregivers with information about a person supported on the person support apparatus 3014 through the signaling and communication system 3012. In one illustrative embodiment, the signaling and communication system 3012 comprises a patient/nurse call system 3012 that, in some embodiments, includes patient stations capable of generating hospital calls and a remote master station which prioritizes and store the calls. One example of such a system is disclosed in U.S. Pat. No. 5,561,412 issued on Oct. 1, 1996 to Novak et al., which is incorporated by reference herein in its entirety. Another example of such a system is disclosed in U.S. Pat. No. 4,967,195 issued on May 8, 2006 to Shipley, which is incorporated by reference herein in its entirety.

In some embodiments, the signaling and communication system 3012 includes a system 3012 for transmitting voice and data in packets over a network with any suitable number of intra-room networks that can couple a number of data devices to an audio station, where the audio station couples the respective intra-room network to a packet based network. One example of such a system is disclosed in U.S. Pat. No. 7,315,535 issued on Jan. 1, 2008 to Schuman, which is incorporated by reference herein in its entirety. Another example of such a system is disclosed in U.S. Patent Publication No. 2008/0095156 issued on Apr. 24, 2008 to Schuman, which is incorporated by reference herein in its entirety.

According to some embodiments, the signaling and communication system 3012 includes a patient/nurse call system, a nurse call/locating badge, an electronic medical record (EMR) database, and one or more computers programmed with work-flow process software. One example of such a system is disclosed in U.S. Patent Publication No. 2008/0094207 published on Apr. 24, 2008 to Collins, Jr. et al., which is incorporated by reference herein in its entirety. Another example of such a system is disclosed in U.S. Patent Publication No. 2007/0210917 published on Sep. 13, 2007 to Collins, Jr. et al., which is incorporated by reference herein in its entirety. Yet another example of such a system is disclosed in U.S. Pat. No. 7,319,386 published on Jan. 15, 2008 to Collins, Jr. et al., which is incorporated by reference herein in its entirety. It should be appreciated that the workflow process software can be the NaviCare® software available from Hill-Rom Company, Inc. It should also be appreciated that the workflow process software can be the system disclosed in U.S. Pat. No. 7,443,303 issued on Oct. 28, 2008 to Spear et al., which is incorporated by reference herein in its entirety. It should further be appreciated that the badge can be of the type available as part of the ComLinx™ system from Hill-Rom Company, Inc. It should also be appreciated that the badge can also be of the type available from Vocera Communications, Inc.

According to some embodiments, the remote signaling and communication system 3012 is configured to organize, store, maintain and facilitate retrieval of bed status information, along with the various non-bed calls placed in a hospital wing or ward, and remotely identify and monitor the status and location of the person support apparatus, patients, and caregivers. One example of such a system is disclosed in U.S. Pat. No. 7,242,308 issued on Jul. 10, 2007 to Ulrich et al., which is incorporated by reference herein in its entirety. It should be appreciated that the remote status and location monitoring can be the system disclosed in U.S. Pat. No. 7,242,306 issued on Jul. 10, 2007 to Wildman et al., which is incorporated by reference herein in its entirety. It should also be appreciated that the remote status and location monitoring can be the system disclosed in U.S. Patent Publication No. 2007/0247316 published on Oct. 25, 2007 to Wildman et al., which is incorporated by reference herein in its entirety.

Figure 2:
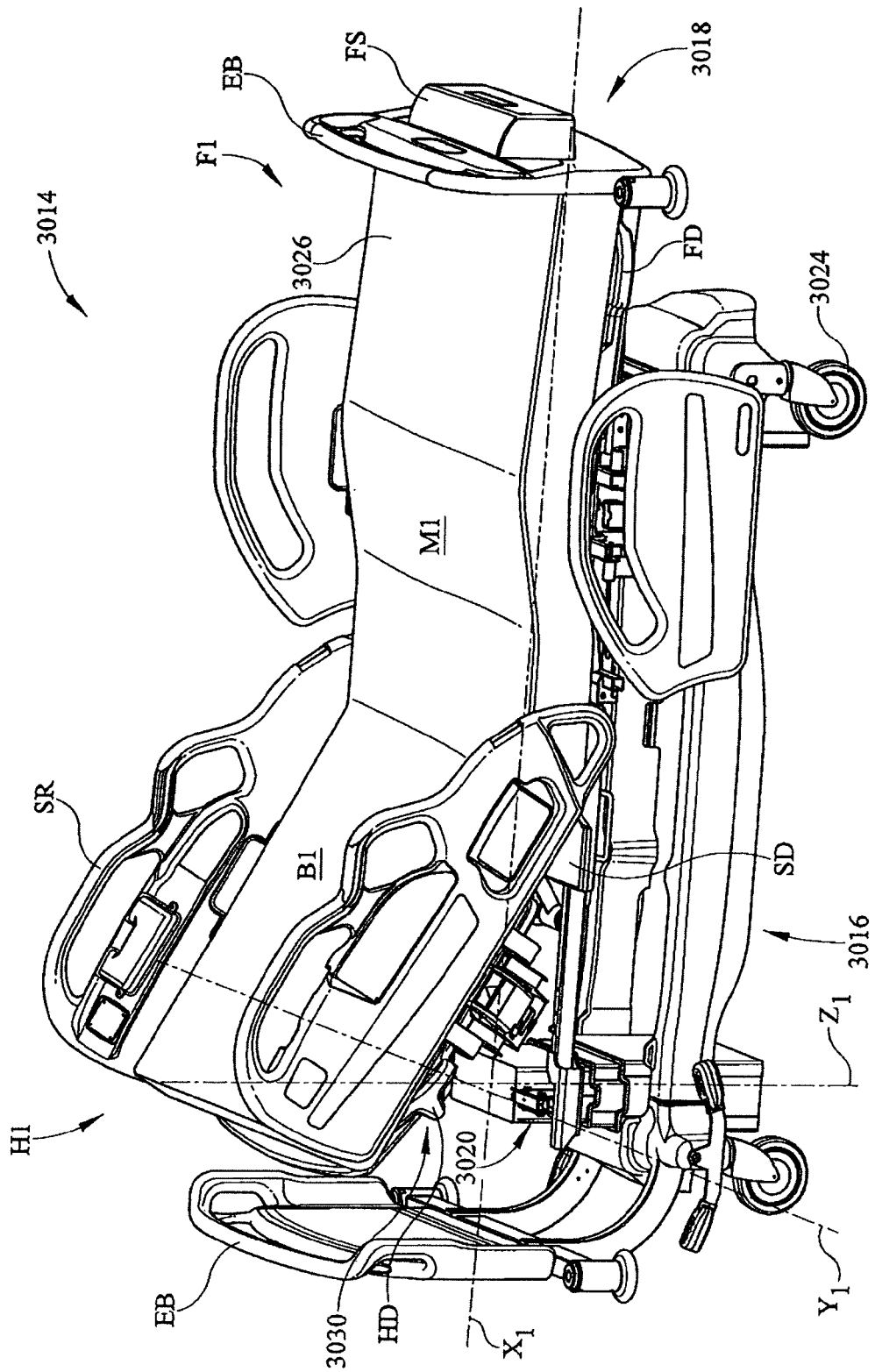
FIG. 2 is a perspective side view of the person support apparatus of the person monitoring system of FIG. 1 according to one illustrative embodiment.

The person support apparatus 3014 according to one illustrative embodiment of the current disclosure is shown in FIG. 2. The person support apparatus 3014 includes a head section H1, where the head and a portion of the torso of a person are to be positioned, and a foot section F1, where the feet of a person are to be positioned. The person support apparatus 3014 includes a lower frame 3016 or base 3016, an upper frame 3018, a plurality of supports 3020, and a control system 3022. It should be appreciated that the person support apparatus 3014 can include only one support 3016. The lower frame 3016 includes at least one lower frame section supported by casters 3024. The supports 3020 are lift mechanisms 3020 that define a vertical axis Z1 which extends through the lower frame 3016 and the upper frame 3018 and are configured to move the upper frame 3018 with respect to the lower frame 3016. It should be appreciated that the supports 3020 can be at least one fixed column (not shown), if desired. It should also be appreciated that, in some embodiments, the supports 3020 move the upper frame 3018 to a Trendelenburg/reverse Trendelenburg position and/or rotate the upper frame 3014 from side to side with respect to the lower frame 3012.

Figure 3:
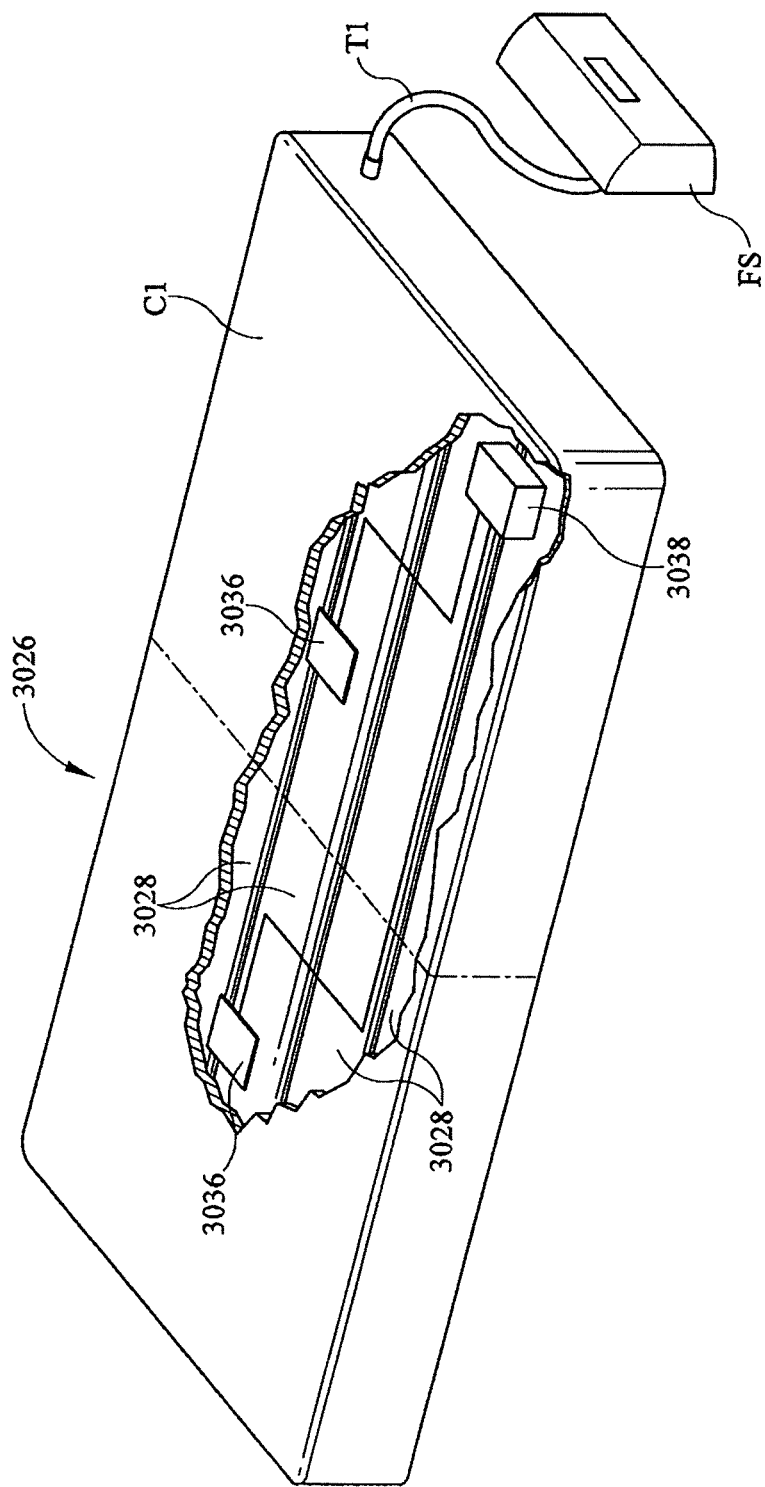
FIG. 3 is a perspective side view of a person support surface that is supported on the person support apparatus of FIG. 2 according to one illustrative embodiment.

The person support apparatus 3014 supports a person support surface 3026 on the upper frame 3018 as shown in FIGS. 2 and 3. The person support surface 3026 is configured to support a person (not shown) in multiple articulated positions. The person support surface 3026 includes a back portion B1 and a main portion M1. The person support surface 3026 includes an outer cover or ticking C1 that covers one or more support sections and/or layers having foam and/or fluid bladders 3028. In some embodiments, the person support surface 3026 delivers therapy to the person, such as, for example, through sequential inflation/deflation of the fluid bladders 3028, rapid changes in pressure of the fluid in the fluid bladders 3028, passing fluid through the person support surface 3026, and/or various other techniques. For example, in various embodiments, one or more portions of the surface 3026 provide alternating pressure therapy, continuous lateral rotation therapy, low air loss therapy, boost assistance, percussion/vibration therapy, and/or other therapies. It should also be appreciated that, in some embodiments, the person support surface 3026 includes a coverlet (not shown) that overlies another person support surface 3026 and is configured to deliver therapy to a person supported thereon. The person support surface 3026 receives fluid from a fluid supply FS connected to the person support surface 3026 by a connecting tube T1. In some embodiments, the fluid supply FS is a gas blower and is configured to vary at least one of a rate and a temperature of fluid supplied to the person support surface 3026.

Figure 4:
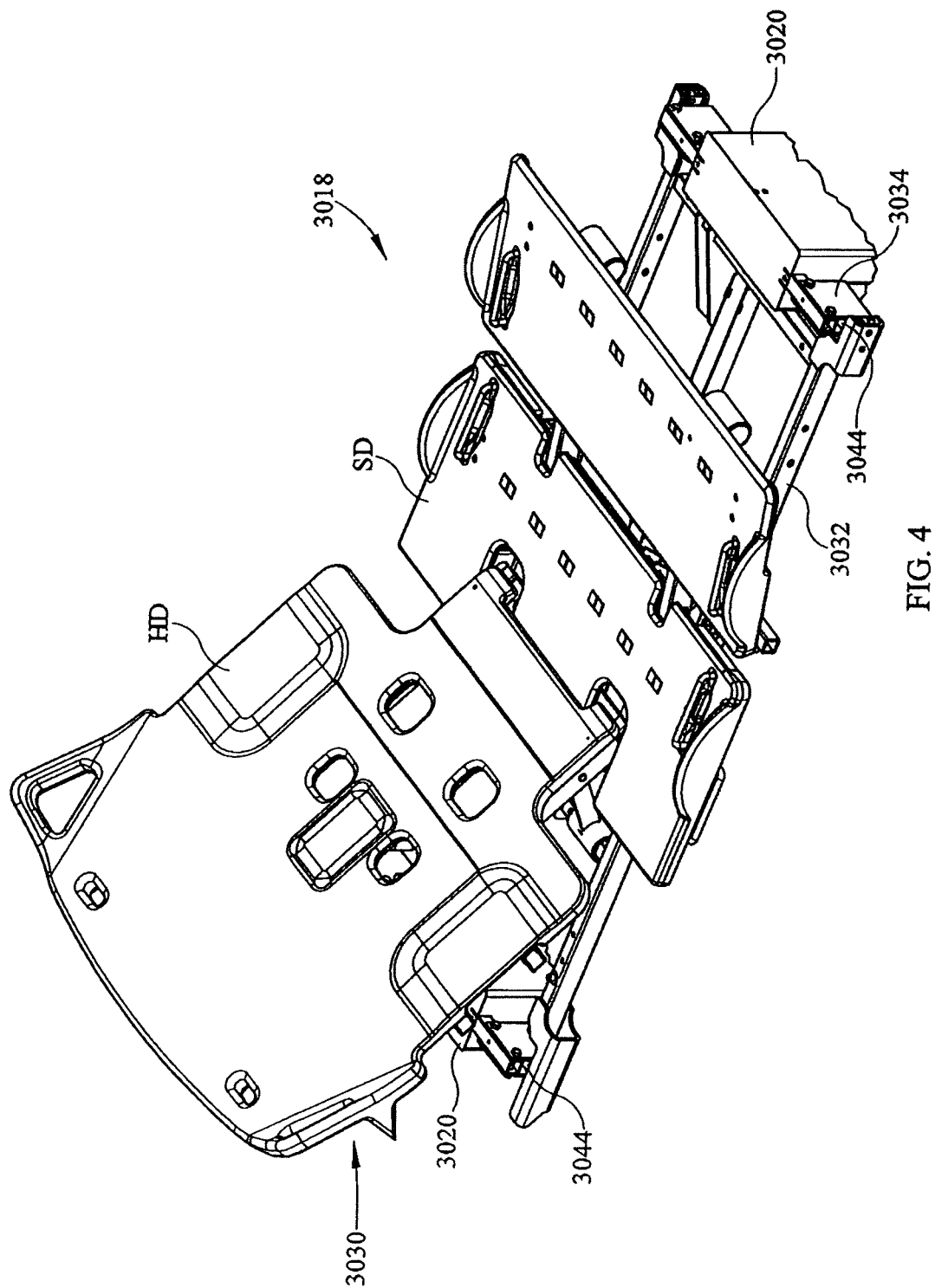
FIG. 4 is a perspective side view of the upper frame of the person support apparatus of FIG. 2 according to one illustrative embodiment.

The upper frame 3018 defines a longitudinal axis X1 that extends at least the length of the person support apparatus 3014 through the head end H1 and the foot end F1 along the lateral center of the upper frame 3018, and a lateral axis Y1 that is perpendicular to the longitudinal axis X1 and extends at least the width of the person support apparatus 3014 through the longitudinal center of the upper frame 3018 as shown in FIGS. 2 and 4. The upper frame 3018 includes a deck 3030, an intermediate frame 3032, and an upper frame base 3034 that couples with the supports 3020 and supports the deck 3030 and the intermediate frame 3032. It should be appreciated that the upper frame 3018 includes a footboard FB, a head board HB, and/or siderails SR in some embodiments. The deck 3030 is comprised of multiple sections, such as, a head deck section HD, a seat deck section SD, and a foot deck section FD, that are pivotably coupled to one another and/or the intermediate frame 3032 and articulate about the lateral axis Y1.

Figure 5:
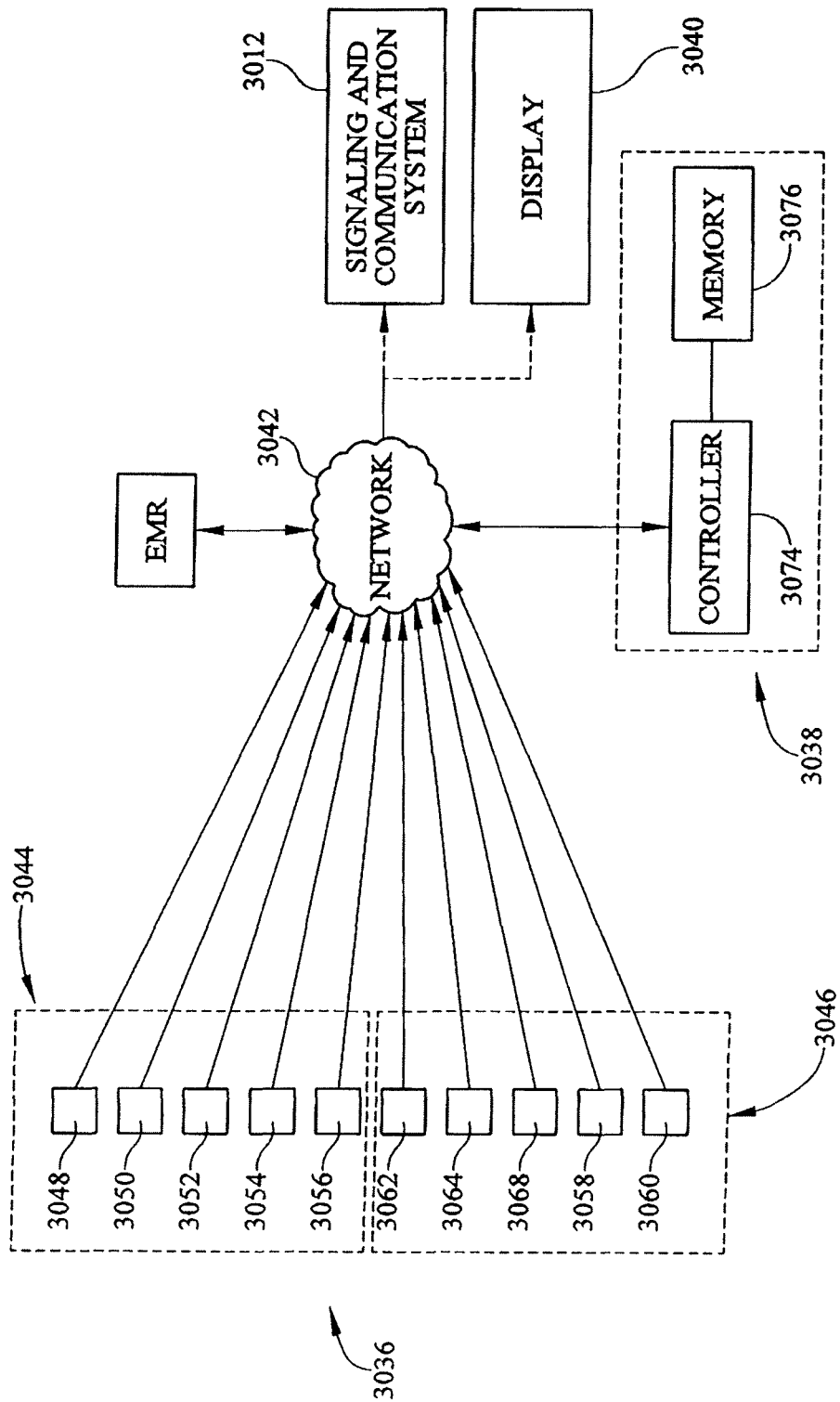
FIG. 5 is diagrammatic view of a control system of the person support apparatus of FIG. 2 according to one illustrative embodiment including a controller and a plurality of sensors.

The control system 3022 is configured to control various functions of the person support apparatus 3014 and/or communicate with the signaling and communication system 3012 as shown in FIG. 5. It should be appreciated that the control system 3022 can be configured to be controlled through the signaling and communication system 3012, if desired. In one illustrative embodiment, the control system 3022 is configured to articulate the deck 3030 with respect to the intermediate frame 3032. In some embodiments, the control system 3022 is configured to administer therapy to a person supported on the person support apparatus 3014. According to some embodiments, the control system 3022 is configured to alert caregivers when a person is exiting the person support apparatus 3014.

The control system 3022 includes a plurality of sensors 3036, control modules 3038, and a display 3040 as shown in FIG. 5. The sensors 3036 and/or the control modules 3038 are coupled to the upper frame 3018 in some embodiments. It should be appreciated that the sensors 3036 and/or the control modules 3038 can be coupled to the lower frame 3016, supports 3020, and/or incorporated within or coupled to the person support surface 3020 in other embodiments, if desired. In one illustrative embodiment, the sensors 3036, control modules 3038, and the display 3040 are directly connected to one another. In another illustrative embodiment, the sensors 3036, control modules 3038, and the display 3040 are operatively connected to one another through a network 3042.

The network 3042 facilitates communication between the various modules 3038, sensors 3036, displays 3040, and/or other equipment operatively connected to the network 3042. In one illustrative embodiment, the network 3042 comprises a CAN network on a person support apparatus 3014. In another illustrative embodiment, the network 3042 is part of the signaling and communication system 3012. In some embodiments, the network 3042 comprises a Serial Peripheral Interface (SPI) network. It should be appreciated that the network 3042 can be other types of networks or communication protocols that can facilitate communication between two or more devices. It should also be appreciated that the module 3038 can be configured to connect to the network 3042 wirelessly, if desired. In one illustrative embodiment, the control module 3038 negotiates with the network 3042 to be a network node. According to some embodiments contemplated by this disclosure, the control modules 3038 can be located at or on any node on the network 3042 and/or distributed across multiple nodes on the network 3042.

In the illustrative example, the sensors 3036 are operatively connected to the control modules 3038 and include sensors that contact the person (contact sensors 3044) and/or sensors that do not contact the person (contact-less sensors 3046) as shown in FIG. 5. In one illustrative embodiment, the contact sensors 3044 contact a person's tissue to measure the desired parameter. In another illustrative embodiment, the contact-less sensors 3046 are integrated into the person support surface 3026. It should be appreciated that the contact-less sensors 3046 can be integrated into the portion of the ticking C1 contacting the person, if desired. In some embodiments, the contact-less sensors 3046 are coupled to at least one of the upper frame 3018, the supports 3020, and/or the lower frame 3016. It should be appreciated that the contact-less sensors 3046 can be coupled to the casters 3024 and/or engaged by the casters 3024, if desired.

The sensors 3036 are configured to sense a variety of parameters, including, but not limited to, for example, a person's physiological information, a position of a person on the person support apparatus 3014 and/or person support surface 3026, a pressure of the fluid inside the bladders 3028 in the person support surface 3026, or other various parameters. In one illustrative embodiment, the contact sensors 3044 include blood pressure sensors 3048 that are configured to sense the person's blood pressure; oxygen saturation level (SpO2) sensors 3050 that are configured to sense the amount of hemoglobin binding sites in the person's bloodstream occupied by oxygen; temperature sensors 3052 that are configured to sense the person's body temperature; heart rate sensors 3054 that are configured to sense the rate at which a person's heart contracts; and respiration rate sensors 3056 that are configured to sense the person's breathing rate as shown in FIG. 5. It should be appreciated that the SpO2 sensors 3050 comprise a pulse oximeter device in some embodiments. It should be appreciated that the contact sensors 3044 are configured to measure other physiological and biochemical parameters in other embodiments.

In some embodiments, the contact-less sensors 3046 include one or more of the following: force sensors 3058 configured to sense the force profile and/or distribution of a person supported on a person support apparatus 3014; pressure sensors 3060 configured to measure the pressure in or among the bladders 3028; temperature sensors 3062 configured to sense the person's body temperature; heart rate sensors 3064 configured to sense the rate at which the person's heart contracts; respiration rate sensors 3066 configured to sense the person's breathing rate; and other sensors configured to sense information corresponding to the status of the person-support apparatus 3014, such as, for example, the angle of the head deck section HD with respect to the longitudinal axis X1 as shown in FIG. 5.

In some embodiments, the force sensors 3058 are load cells 3058 that couple the intermediate frame 3032 to the upper frame base 3034 proximate the corners of the upper frame 3018 and are configured to measure the weight of a person on the person support apparatus 3014. Alternatively or additionally, the force sensors 3058 comprise piezoelectric sensors and/or elongated sensor strips or arrays 3058 in some embodiments. In some embodiments, the pressure sensors 3060 are coupled between the bladders 3028 such that they allow communication between adjacent bladders 3028. In some embodiments, pressure sensors 3060 are situated within the bladders 3028 and measure the pressure within the bladder 3028.

In some embodiments, the heart rate sensors 3064 and respiration rate sensors 3066 are integrated into the surface 3026. In some embodiments contemplated herein, the heart rate sensors 3064 and respiration rate sensors 3066 are force sensors 3058 and/or pressure sensors 3060. It will be appreciated that the sensors 3036 are configured to sense various other physiological characteristics. In some embodiments, the heart rate sensors 3064 and respiration rate sensors 3066 are pressure-strip sensors disposed on the fluid bladders 3028 along an axis parallel to the lateral axis Y1 and/or along an axis parallel to the longitudinal axis X1.

The control modules 3038 can each be configured to perform different operations, if desired. According to this disclosure, a single control module 3038 can be configured to perform the multiple different operations if desired. Optionally, a single control module 3038 can be configured to perform operations independently or in conjunction with at least one other control module 3038. In one contemplated embodiment, one control module 3038, such as, a person position monitor module (not shown) (PPM), is configured to detect the position of a person on the person support apparatus 3014. Alternatively or additionally, a second control module 3038, such as a therapy control module (not shown), is configured to sense and/or modify the pressure within the fluid bladders 3028. Optionally, a third control module 3038, such as a physiological parameter monitor (not shown), is configured to detect a person's physiological information. In some embodiments, a fourth control module 3038, such as a wake up detector (not shown), is configured to detect when a person is regaining consciousness.

The control modules 3038 are implemented using software or hardware. In some embodiments, the control modules 3038 are implemented in software and are configured to perform one or more operations. In some embodiments, for example, the modules 3038 are configured to communicate via a memory mailbox where information from one module is sent to the memory address of a recipient module. In other embodiments, the software modules are configured to push information in a memory location, such as, a stack, that the control modules 3038 monitor or periodically check for information that the software modules subscribe to.

In contemplated embodiments, the control module 3038 is implemented using hardware. The control module 3038 includes a controller 3074 or processor 3074 and memory 3076 as shown in FIG. 5. The controller 3074 is provided as a single component or a collection of operatively coupled components; and can be comprised of digital circuitry, analog circuitry, or a hybrid combination of both of these types. When of a multi-component form, controller 3074 has one or more components remotely located relative to the others. The controller 3074 can include multiple processing units arranged to operate independently, in a pipeline processing arrangement, in a parallel processing arrangement, and/or such different arrangement as would occur to those skilled in the art.

In some embodiments, processor 3074 is a programmable microprocessing device of a solid-state, integrated circuit type that includes one or more processing units and memory. The controller 3074 can include one or more signal conditioners, modulators, demodulators, Arithmetic Logic Units (ALUs), Central Processing Units (CPUs), limiters, oscillators, control clocks, amplifiers, signal conditioners, filters, format converters, communication ports, clamps, delay devices, memory devices, and/or different circuitry or functional components as would occur to those skilled in the art to perform the desired communications. In some embodiments, the controller 3074 includes a computer network interface to communicate among various system components and/or components not included in the depicted system, as desired. The listed examples are not intended to be an exhaustive list of structures that are within the scope of controller 3074, but are instead only a non-exhaustive list of such structures which can have substantial differences in the manner in which they are implemented and/or operate.

The controller 3074 is configured to receive input signals corresponding to signals from the sensors 3036 and/or output signals from other modules 3038 via the network 3042. The information is stored in the memory 3076, which is operatively coupled to the controller 3074 as shown in FIG. 5. It should be appreciated that the memory 3076 is integrated into the controller in some embodiments. The controller 3074 is configured to execute operating logic 3078 that defines various control, management, and/or regulation functions. This operating logic 3078 can be in the form of software, firmware, and/or dedicated hardware, such as, a series of programmed instructions, code, electronic files, or commands using general purpose or special purpose programming languages or programs that are executed on one or more general purpose or special purpose computers, processors, other control circuitry, or networks; a hardwired state machine; and/or a different form as would occur to those skilled in the art.

Figure 6:
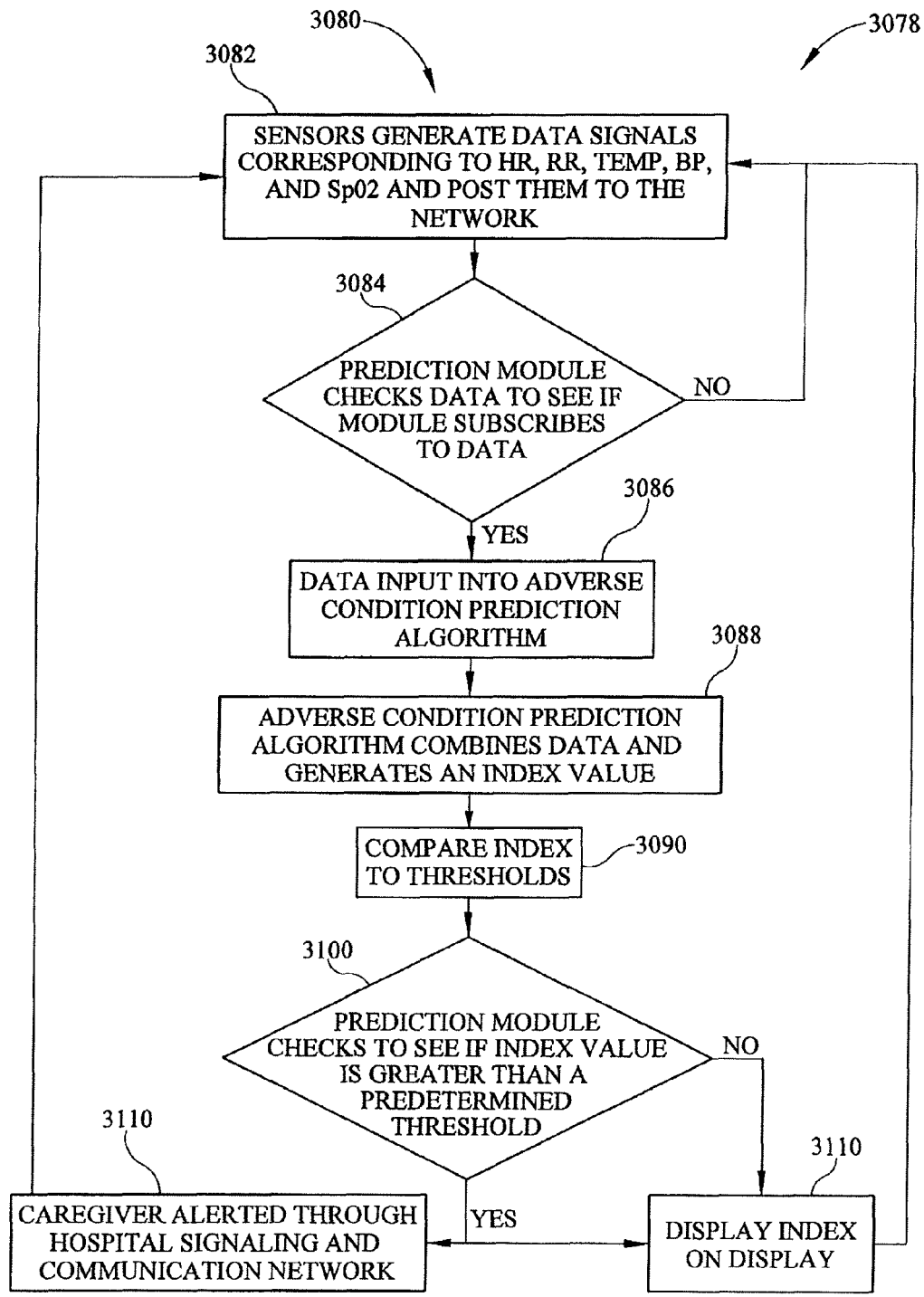
FIG. 6 is a flow chart illustrating a procedure that can be executed by the controller of the control system of FIG. 5 according to one illustrative embodiment.

In the illustrative embodiment, the controller 3074 includes operating logic 3078 in the form of procedure 3080, for example, as shown in the flowchart of FIG. 6. Procedure 3080 includes operations/conditionals shown at blocks 3082, 3084, 3086, and 3088. Procedure 3080 is used to generate a condition score corresponding to the condition of a person, which is compared to a threshold in order to predict the onset of an adverse condition.

The thresholds are established in accordance with hospital specific standard protocols and/or are generic thresholds that can be modified as desired. In some embodiments, the preset thresholds that are set by standard hospital specific protocols, which are automatically selected based on information present in a person's electronic medical record (EMR), in patient profiles, and/or based on the condition score generated by the procedure 3080. Alternatively or additionally, the thresholds are set by a caregiver through an interface (not shown) on the person-support apparatus 3014 by manually selecting the protocols or modifying the generic thresholds. In some contemplated embodiments, the thresholds are automatically modified based on information in the person's electronic medical record (EMR). It should be appreciated that the thresholds can be person specific and can be incorporated into the person's EMR. It should also be appreciated that the thresholds can be incorporated into a patient profile that can be used for multiple people with similar characteristics. In some embodiments, the thresholds are modified by a caregiver through the signaling and communication system 3012.

Illustrative procedure 3080 begins with operation 3082 where, in one illustrative embodiment, the sensors 3036 generate data signals corresponding to one or more of heart rate (HR), respiration rate (RR), temperature (TEMP), blood pressure (BP) or pulse oximetry (SpO2) and post them to the network. In some embodiments, the predetermined threshold is modified by the status of a care facility. For example, the predetermined threshold is modified by one or more of the staffing level of the facility, the time of day, the day of the week, whether the day is a holiday, what the acuity of the person is, what the acuity of the other people in the hospital is, the location of the caregiver with respect to the person, where the caregiver is in their rounds with respect to the person, the amount of people in the facility, the size of the facility, the work-flow status of the facility, the amount of procedures taking place and/or the time they begin and/or the duration of the procedure, or other information regarding the facility and facility staff. Modifying the threshold based on the status of the care facility information can help increase the accuracy of the threshold if, for example, staffing levels are lower or if adverse events are more prone to occur while the patient is asleep (i.e., time of day). Also, if a calculated condition score is within a predetermined amount of the predetermined threshold, additional staff could be deployed to an area near the patient, or redeployed to move closer to patient, or the frequency of caregiver visits to patient can be increased to position caregivers in close proximity to the patient. This could help reduce the number of false alerts.

In some contemplated embodiments, the predetermined threshold is modified by the status of the person-support apparatus 3014. For example, the predetermined threshold is modified by one or more of the height of the upper frame 3018, the angle at which a section of a deck 3030 is with respect to the upper frame 3018, the position of the siderail SR, at least one of the Trendelenburg position and the reverse Trendelenburg position, the status of the CPR function, the center of gravity of the person-support apparatus 3014 and/or the person supported thereon, the position of a person on the person-support apparatus 3014, the status of the alarms on the person-support apparatus 3014, and/or other information about the person-support apparatus 3014. Modifying the threshold based on the status of the person-support apparatus 3014 can help increase the accuracy of the threshold if, for example, a person is classified as a fall risk and the person-support apparatus 3014 is 36 inches above the floor, or less acute if, for example, the person is classified as a fall risk and the person-support apparatus 3014 is 12 inches off the floor. In some embodiments, the person does not need to be classified as a fall risk. Also, the threshold can be made more acute if, for example, the person-support apparatus 3014 is in a Trendelenberg configuration and the person is prone to sliding down (out of a therapeutic position). In some embodiments, the person does not need to be prone to sliding down. This could help reduce the number of false alerts.

In some embodiments, the predetermined threshold is modified by the person's history. For example, the predetermined threshold is modified by one or more of a person's preferences, a person's tendencies, a person's electronic medical records (EMR), a pressure ulcer risk assessment of a person, a medical history of a person, an allergy of a person, a medical condition of a person, a diagnosis of a person, a medication chart for a person, a caregiver assignment history for a person, a habit of a person, and other information about the person. Modifying the threshold based on the status of the person's history can help increase the accuracy of the threshold if, for example, the person is classified as a fall risk or is more apt to fall out of bed, or is prone to developing pressure ulcers or might be at an elevated risk for developing pressure ulcers. This could help reduce the number of false alerts.

In some contemplated embodiments, the predetermined threshold is modified by the status of the support surface 3026 For example, the predetermined threshold is modified by one or more of the fluid pressure in the fluid bladder 3028, the status of a surface therapy, the status of a low-air loss therapy, the status of a percussion vibration therapy, the status of a lateral rotation therapy, the status of an alternating pressure therapy, the status of a zone of the person-support surface 3026, the status of a person-support surface function, the status of a person-support surface length extension function, the status of a person-support surface length reduction function, the status of a person-support surface width extension function, the status of a person-support surface width reduction function, the status of a turn assist function, the position of a person on the person-support surface 3026, the morphology of a person on the person-support surface 3026, or other information about the person-support surface 3026. Modifying the threshold based on the status of the support surface 3026 can help reduce the amount of false calls due to dynamics of support surface functions.

In some embodiments, the predetermined threshold is modified by the input from the interface, i.e., user interface. Modifying the threshold based on inputs from the user interface can help improved functionality of the system by permitting the user to optimize based upon a condition that has not been predetermined.

Procedure 3080 begins with operation 3082 where the sensors 3036 post electronic data signals corresponding to at least one of an event and an amount on the network 3042. In some embodiments, the sensors 3036 post electronic data signals to a memory mailbox or register (not shown) where the modules 3038 are implemented in software. In some embodiments, sensors 3036 post data signals substantially continuously and, in other embodiments, sensors 3036 post data signals at predetermined intervals. The data signals from sensors 3036 are representative of heart rate, respiration rate, temperature, blood pressure and/or SpO2 as indicated at block 3082 of FIG. 6. Data signals corresponding to features of the person support apparatus 3014 are also posted to the network such as, for example, signals from force sensors 3044 of a patient position and/or movement monitoring system of apparatus 3014 and are used in a similar manner as signals from sensors 3036 in procedure 3080.

In the conditional of block 3084, the controller 3074 examines each of the data signals posted by the sensors 3036 on the network 3042 and determines if the associated module 3038 subscribes to the data. If the module 3038 does not subscribe to the data, then the algorithm returns to block 3082 and awaits more incoming data.

If at block 3084 it is determined that module 3038 subscribes to the data, the algorithm proceeds to the operation of block 3086 and the data is input into an algorithm that is used to predict an adverse event or condition. In some embodiments, the data signals can be used to select one or more standard hospital specific protocols, which, in some instances, have predetermined thresholds associated therewith. Alternatively or additionally, the data signals can be input into an algorithm that is used to select the hospital specific protocols and/or to set the predetermined thresholds associated with the protocols.

In the operation of block 3088, the controller 3074 executes the algorithm to generate a condition score corresponding to the condition of the person and/or to generate a graphic representative of the condition of the person. In one embodiment, the algorithm receives inputs from the contactless sensors 3046 corresponding to the heart rate, respiration rate, and temperature of a person, and inputs from the contact sensors 3044 corresponding to the blood pressure and SpO2 of a person. It should be understood that all of the inputs can be from the contact sensors 3044 in other embodiments. The controller 3074 processes the data inputs in accordance with the algorithm to calculate the condition score and/or generate the graphic.

In some embodiments, the algorithm combines the inputs into a data point, which is used to calculate a condition score constituting a one-dimensional visualization space based on the distance of the data point in a multi-dimensional measurement space, whose coordinates are defined by values of the inputs, from a normal point. In some embodiments, the inputs are weighted such that an input deemed to be more important than another has more influence on the resulting data point and/or condition score. The weight assigned to the inputs are modified based on at least one of a status of a care facility, a status of the person-support apparatus 3014, a status of the person-support surface 3026, a history of a person supported on the person-support surface 3026, and a user input as previously described above. In other contemplated embodiments, the algorithm maps the inputs from an n-dimensional measurement space to an m-dimensional visualization space using a dimensionality reduction mapping technique, and displays the m-dimensional visualization space on the display 3040. One example of such a system using this algorithm and technique is disclosed in U.S. Pat. No. 7,031,857 issued on Apr. 18, 2006 to Tarassenko et al., which is hereby incorporated by reference herein in its entirety. One condition score in accordance with the teachings of U.S. Pat. No. 7,031,857 is know as a Visensia® index that can be produced by the Visensia® system sold by OBS Medical, for example. The Visensia® index creates a score based on heart rate, respiration rate, blood pressure, temperature, and SpO2 data.

Based on the foregoing, it will be understood that the Visensia® index is a condition score that is based on, or a function of, only a person's physiological data. According to this disclosure, some or all of the physiological data used to calculate the Visensia® index is obtained by one or more sensors included as part of the person support apparatus 3014. This distinguishes over the known prior art. To the extent that some of the physiological data needed to calculate a condition score, such as the Visensia® index, is obtained by equipment and/or sensors that are not included as part of person support apparatus 3014, such data is transmitted to controller 3074 in accordance with this disclosure for the purpose of calculating the condition score. For example, data is transmitted to controller 3074 from a person's EMR in some instances as suggested diagrammatically in FIG. 5. In other instances, person support apparatus 3014 is communicatively coupled to physiological monitoring equipment that is co-located with apparatus 3014 to obtain the needed data for calculating a condition score. In the preceding examples, controller 3074 automatically initiates the queries to obtain the needed data from the EMR or co-located equipment and/or picks up the needed data from network transmissions. Thus, controller 3074 automatically calculates the condition score without the need for any further actions on the part of caregivers or users. However, it is within the scope of this disclosure for some or all of the needed physiological data to be entered by a caregiver using a user interface of the apparatus 3014.

In another contemplated embodiment, the condition score comprises a modified early warning score (MEWS). According to this disclosure, the data needed to calculate the MEWS is obtained from sensors included as part of person support apparatus 3014, obtained via manual user inputs, obtained from separate monitoring equipment that communicates with controller 3074 of apparatus 3014, and/or obtained from the person's EMR. The MEWS is a known score calculated based on the following table:

| | Score | | | | | | |
|---|---|---|---|---|---|---|---|
| | 3 | 2 | 1 | 0 | 1 | 2 | 3 |
| Systolic BP | <70 | 71-80 | 81-100 | 101-199 | — | >200 | — |
| Heart rate (BPM) | — | <40 | 41-50 | 51-100 | 101-110 | 111-129 | >130 |
| Respiratory rate (RPM) | — | <9 | — | 9-14 | 15-20 | 21-29 | >30 |
| Temperature (° C.) | — | <35 | — | 35.0-38.4 | — | >38.5 | — |
| AVPU | — | — | — | A | V | P | U |

In the MEWS table, the various integers in the column headings are added together based on the various readings for the person of the data corresponding to the rows of the table. A score of 5 or greater indicates a likelihood of death. With regard to the systolic blood pressure, heart rate, respiratory rate, and temperature portions of the MEWS, those pieces of information are obtained using sensors 3036 of person support apparatus 3014 and/or using the other manners of obtaining a person's physiological data as discussed above. It is contemplated by this disclosure that the AVPU portion of the MEWS is obtained using information from the person support apparatus 3014 as discussed below.

The AVPU portion of the MEWS indicates whether a person is alert (A), responsive to voice (V), responsive to pain (P), or unresponsive (U). As discussed above, the person support apparatus 3014 in some embodiments comprises a hospital bed having a patient position monitoring system including sensors, such as load cells, piezoelectric sensors, and/or force sensitive resistors (FSR's) which sense a patient's position and/or movement. In accordance with this disclosure, the patient movement information is used by the controller to automatically assign an appropriate integer corresponding to the A portion or the U portion of the AVPU line of the MEWS depending upon the amount of movement of the patient. For example, if the patient has not moved for a threshold amount of time, such as fifteen minutes or an hour or some threshold greater than or less than these particular times, then the integer associated with the U portion of the AVPU line of the MEWS is assigned automatically by controller 3074. If the patient has moved by a threshold amount within a particular time period, then the integer associated with the A portion of the AVPU line of the MEWS is assigned automatically by controller 3074.

It is contemplated by this disclosure that the controller 3074 initiates a voice query to the person in some embodiments. If the person answers the voice query orally or by engaging a designated user input, such as pressing a particular button mentioned in the voice query, then the controller 3074 automatically assigns an appropriate integer corresponding to the V portion of the MEWS. The voice query is a pre-recorded message in some embodiments. The voice query is initiated by controller 3074 if the person has been inactive for the threshold period of time. In other words, in some embodiments, the voice query is initiated only after the conditions for assigning the U portion of the MEWS has been satisfied. Thus, if the person responds properly to the voice query, the AVPU portion of the MEWS is assigned as V rather than U. Apparatus 3014, therefore, has speakers or similar such sound-producing devices through which the voice query is played and, in some instances, a microphone that picks up the person's oral response. Appropriate interactive voice recognition (IVR) software is provided in such embodiments.

With regard to determining whether to select the P portion of the AVPU line of the MEWS score, apparatus 3014 is operated to inflict some amount of discomfort to the patient and then monitors the person's response, such as an oral response or movement. For example, in some embodiments, apparatus 3014 includes an inflatable cuff or sleeve placed on a limb of the person and the controller 3074 controls inflation and deflation of the cuff or sleeve. If the patient movement information indicates sufficient patient movement by the patient in response to inflation of the cuff or sleeve, then the controller automatically assigns the appropriate integer corresponding to the P portion of the AVPU line of the MEWS. Alternatively or additionally, a microphone is used to determine if the patient expresses an audible pain or discomfort sound at which point the integer associated with the P portion of the AVPU line of the MEWS is assigned. The steps for determining whether to assign the P integer are performed only after the steps for determining whether to assign the U integer and/or the V integer in some embodiments. That is, operating the person apparatus 3014 so as to cause the patient some discomfort is only done as a last resort. In assigning the AVPU integer in the MEWS, it will be appreciated that it is the lowest pertinent integer that is assigned. Clearly, an alert person would also be responsive to voice for example.

The MEWS and Visensia® index discussed above are just a couple of examples of condition scores according to this disclosure. The teachings of this disclosure are intended to be broadly applicable to all types of condition scores.

Referring once again to FIG. 6, in the operation of block 3090, the controller 3074 compares the calculated condition score (referred to sometimes in FIG. 6 as an "index value" or simply an "index") with the predetermined thresholds to determine at least one of the likelihood that an adverse condition will occur, an amount of time before an adverse condition will occur, and/or how close the condition score is to the threshold.

In the conditional of block 3100, if the controller 3074 determines that the condition score is greater than the threshold, then, in one illustrative embodiment, a status update including the condition score is communicated to a caregiver through the signaling and communication system 3012 and/or is displayed on the display 3040 as indicated at block 3110. That is, if the condition score exceeds the threshold, then, in some embodiments, at least one of the condition score and an alert signal are communicated to a caregiver. In other embodiments, the alert condition may correspond to the condition score being less than, rather than greater than, a particular threshold. The term "greater than" is intended to cover one or both of a greater than situation and a greater than or equal to situation and the term "less than" is intended to cover one or both of a less than situation and a less than or equal to situation. In some contemplated embodiments, the frequency of the alerts can be adjusted based on one or more of the user input, the acuity level of the person, the status of the care facility, the status of the person-support apparatus 3014, the status of the person-support surface 3026, the history of the person, and other information.

As alluded to above, in some embodiments, the condition score and/or alert signal are communicated to a caregiver through the signaling and communication system 3012. Alternatively or additionally, the condition score and/or alert signal are displayed on the display 3040. In still other embodiments, the condition score and/or alert signal are communicated to the Visensia® Alert system sold by OBS Medical. In further embodiments, the condition score is communicated to and stored in the person's EMR.

The display 3040 is any suitable display such as a liquid crystal display, touch screen display, plasma screen, light emitting diode display, cathode ray tube display, or other conventional display. The display 3040 is operable to display multiple parameters thereon along with the condition score in some embodiments. In some contemplated embodiments, the display 3040 displays physiological and/or biochemical information sensed by contact sensors 3044 along with the condition score. Thus, it is within the scope of this disclosure for the display 3040 to display physiological and/or biochemical information on the display 3040 along with the condition score. In yet other embodiments, the display 3040 displays bed status information and/or graphics, for example, a head deck section HD angle or PPM armed indicator, on the display along with the condition score. In still other contemplated examples, the display 3040 displays bed status information and/or graphics along with patient condition graphics, such as, pie charts. Other information that is displayable on the display 3040 includes force profile information and/or graphics, person position information and/or graphics, weight, and other physiological information.

Figure 7:
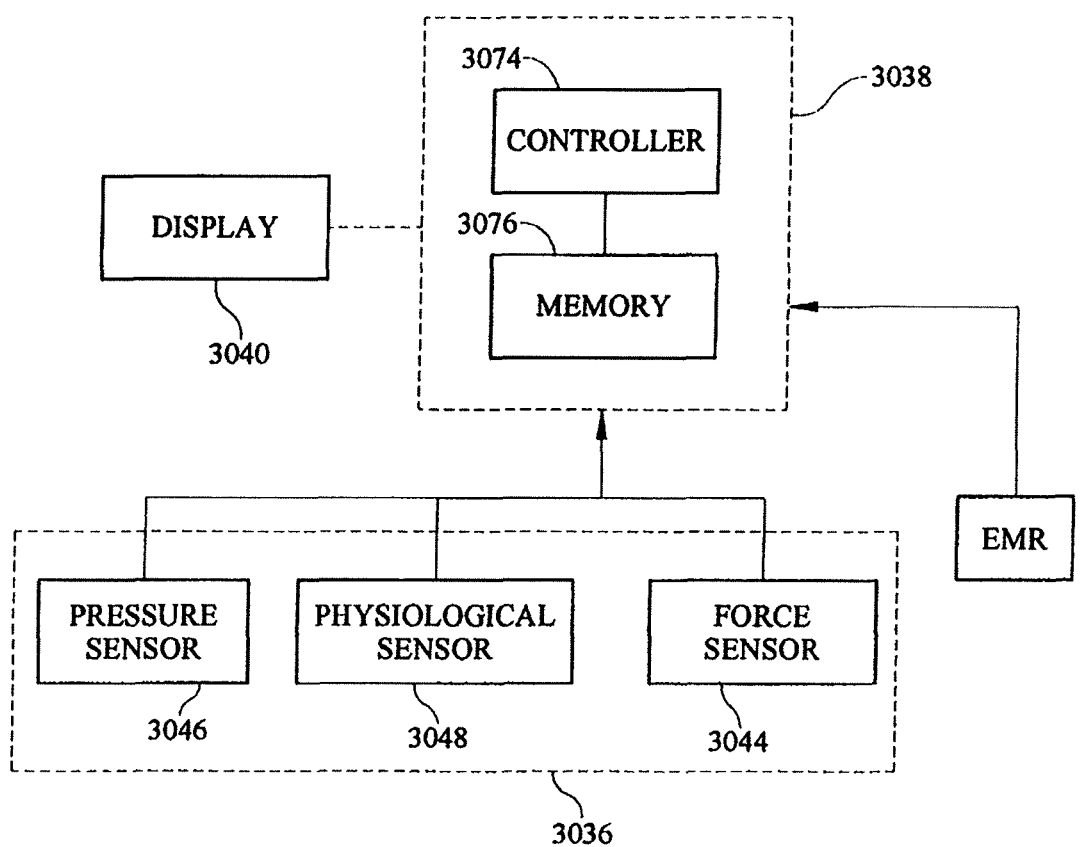
FIG. 7 is a diagrammatic view of a control system of the person support apparatus of FIG. 2 according to one illustrative embodiment including a controller and a plurality of sensors.

Referring now to FIG. 7, the sensors 3036 are operatively coupled to the control modules 3038 and are configured to sense various parameters, including, but not limited to, for example, a person's physiological information, a position of a person on the person support apparatus 3014 and/or person support surface 3026, a pressure of the fluid inside the bladders 3028 in the person support surface 3026, or other various parameters. As mentioned above, the sensors 3036 can be sensors configured to contact the tissue of a person and/or sensors configured to not contact the tissue of a person. In some embodiments, the sensors 3036 are force sensors 3044 coupled to the upper frame 3018 and are configured to measure force on the upper frame 3018 as shown in FIGS. 4 and 7. In some embodiments, the sensors 3036 are force sensors 3044 that measure force on the upper frame 3018 and are positioned between the intermediate frame 3032 and the upper frame base 3034 so as to couple the intermediate frame 3032 and deck 3030 to the upper frame base 3034.

In some contemplated embodiments, the sensors 3036 are force sensors 3044 integrated into the person support surface 3026 and configured to measure changes in force on the person support surface 3026 as shown in FIG. 4. Alternatively or additionally, the force sensors 3044 are coupled to the supports 3020 and/or the lower frame 3016. Sensors 3044 integrated into the casters 3024 and/or engaged by the casters 3024 are also within the scope of this disclosure. In some embodiments, the force sensors 3044 are load cells that are coupled proximate the corners of the intermediate frame 3032. In other embodiments, the sensors 3044 are piezoelectric sensors and/or elongated sensor strips or arrays 3038. It will be appreciated that the force sensors 3044 comprising other force sensor types can be provided and positioned in other locations on the upper frame 3018 and/or within the person support surface 3026.

In some embodiments, the sensors 3036 are pressure sensors 3046 integrated into the person support surface 3026 and configured to measure the pressure in or among the fluid bladders 3028 in the person support surface 3026 as shown diagrammatically in FIG. 7. The pressure sensors 3046 are coupled between the bladders 3028 in some embodiments such that they can allow communication between adjacent bladders 3028. It should be appreciated that the pressure sensors can be situated within the bladders 3028 and/or otherwise positioned to measure the pressure within the bladder 3028. Pressure sensors 3046 coupled to bladders 3028 via pneumatic tubes, hoses, or other types of conduits are contemplated by this disclosure as well.

In some embodiments, the sensors 3036 are physiological sensors 3048 integrated into the person support surface 3026 and configured to measure various physiological parameters of a person supported on the person support surface 3026 as suggested in FIG. 7. Optionally, the physiological sensors 3048 can be coupled to the upper frame 3018, the supports 3020, and/or the lower frame 3016 in lieu of being coupled to the mattress 3046. As indicated above, the force sensor 3044 and/or pressure sensor 3046 are configured to sense physiological parameters in some embodiments. For example, one or more of the physiological sensors 3048 are used to sense the heart rate and/or respiration rate of a person supported on the person support surface 3026 in some embodiments. Alternatively or additionally, one or more of the physiological sensors 3048 are configured to sense the temperature of the person. In some embodiments, the physiological sensors 3048 are configured to sense the weight of the person on the person support surface 3026. In some embodiments, the physiological sensors 3048 are pressure-strip sensors disposed on the fluid bladders 3028 along an axis parallel to the lateral axis Y1 and/or along an axis parallel with the longitudinal axis X1.

In some embodiments, one or more of the sensors 3036 produces an analog data signal and is connected directly to the controller 3074. In other embodiments, one or more of the sensors 3036 produce a digital data signal, e.g., a serial digital data signal, and are connected to the network 3042, e.g., SPI network, to communicate with the controller 3074. The data signals can be stored in the memory 3076, which is operatively coupled with the controller 3074. As mentioned above, the memory 3076 is integrated into the controller 3074 in some embodiments.

In some embodiments, the controller 3074 executes operating logic that defines various control, management, and/or regulation functions. This operating logic can be in the form of software, firmware, and/or dedicated hardware, such as, a series of programmed instructions, code, electronic files, or commands using general purpose or special purpose programming languages or programs that can be executed on one or more general purpose or special purpose computers, processors, other control circuitry, or networks; a hardwired state machine; and/or a different form as would occur to those skilled in the art.

Any theory, mechanism of operation, proof, or finding stated herein is meant to further enhance understanding of principles of the present disclosure and is not intended to make the present disclosure in any way dependent upon such theory, mechanism of operation, illustrative embodiment, proof, or finding. It should be understood that while the use of the word preferable, preferably or preferred in the description above indicates that the feature so described can be more desirable, it nonetheless can not be necessary and embodiments lacking the same can be contemplated as within the scope of the disclosure, that scope being defined by the claims that follow.

In reading the claims it is intended that when words such as "a," "an," "at least one," "at least a portion" are used there is no intention to limit the claim to only one item unless specifically stated to the contrary in the claim. When the language "at least a portion" and/or "a portion" is used the item can include a portion and/or the entire item unless specifically stated to the contrary.

While embodiments of the disclosure have been illustrated and described in detail in the drawings and foregoing description, the same are to be considered as illustrative and not restrictive in character, it being understood that only the selected embodiments have been shown and described and that all changes, modifications and equivalents that come within the spirit of the disclosure as defined herein or by any of the following claims are desired to be protected.

The invention claimed is:

1. A person-support structure comprising
a control system,
an input configured to communicate a first input signal to the control system,
a sensor configured to sense a physiological characteristic of a person supported on the person-support structure and communicate a second input signal corresponding to the physiological characteristic to the control system,
the control system configured to calculate a condition score as a function of the first input signal and the physiological characteristic of the person and compare the condition score to a predetermined threshold, the control system further configured to cause an alert signal to be output when the condition score is greater than the predetermined threshold, wherein the control system scales at least one of the physiological characteristic of the person and the predetermined threshold as a function of the first input signal, wherein the person-support structure includes a bed frame having an upper frame movably supported above a lower frame and the input includes a second sensor coupled to the bed frame and configured to sense a status of the bed frame, the first input signal including information corresponding to the status of the bed frame.

2. The person-support structure of claim 1, wherein the input further comprises a user interface configured to receive a user input, the first input signal including information relating to the user input.

3. The person-support structure of claim 1, wherein the person-support structure includes a person-support surface and the input includes a third sensor coupled to the person-support surface and configured to sense a status of the person-support surface, the first input signal including person-support surface status information.

4. The person-support structure of claim 3, wherein the status of the person-support surface includes at least one of a pressure in a fluid bladder of the person-support surface, a status of a surface therapy, a status of a low-air loss therapy, a status of a percussion vibration therapy, a status of a lateral rotation therapy, a status of an alternating pressure therapy, a status of a surface zone, a status of a surface function, a status of a surface length extension function, a status of a surface length reduction function, a status of a surface width extension function, a status of a surface width reduction function, a status of a turn assist function, a position of a person on the person-support surface, and a morphology of a person on the person-support surface.

5. The person-support structure of claim 1, wherein the first input signal includes information corresponding to the history of a person.

6. The person-support structure of claim 5, wherein the history of the person includes at least one of a preference of a person, a tendency of a person, an electronic medical record (EMR) of a person, a pressure ulcer risk assessment of a person, a medical history of a person, an allergy of a person, a medical condition of a person, a diagnosis of a person, a medication chart for a person, a caregiver assignment history for a person, and a habit of a person.

7. The person-support structure of claim 1, wherein the status of the bed frame includes at least one of a height of the upper frame, an angle at which a section of a deck movably coupled to the upper frame is with respect to the upper frame, a position of a siderail, at least one of a Trendelenburg position and reverse Trendelenburg position, a CPR function status, a center of gravity of a person on the bed frame, a position of the person on the bed frame, and a status of a person-support alarm.

8. The patient-support structure of claim 1, wherein the control system is configured to communicate with a remote system.

9. The patient-support structure of claim 8, wherein the remote system comprises a nurse call system.

10. A person-support structure comprising
a control system,
an input configured to communicate a first input signal to the control system,
a sensor configured to sense a physiological characteristic of a person supported on the person-support structure and communicate a second input signal corresponding to the physiological characteristic to the control system,
the control system configured to calculate a condition score as a function of the first input signal and the physiological characteristic of the person and compare the condition score to a predetermined threshold, the control system further configured to cause an alert signal to be output when the condition score is greater than the predetermined threshold, wherein the control system scales at least one of the physiological characteristic of the person and the predetermined threshold as a function of the first input signal, wherein the first input signal includes information corresponding to a characteristic of a care facility.

11. The person-support structure of claim 10, wherein the characteristic of the care facility includes at least one of a staffing level of the care facility, at least one of a date and a time of day, an amount of people in the care facility, a size of the care facility, a location of a caregiver within the care facility, a progress of a caregiver on their rounds, and an acuity of people in the care facility.

12. The person-support structure of claim 10, wherein the person-support structure includes a bed frame having an upper frame movably supported above a lower frame and the input includes a second sensor coupled to the bed frame and configured to sense a status of the bed frame, the first input signal including information corresponding to the status of the bed frame.

13. The person-support structure of claim 12, wherein the status of the bed frame includes at least one of a height of the upper frame, an angle at which a section of a deck movably coupled to the upper frame is with respect to the upper frame, a position of a siderail, at least one of a Trendelenburg position and reverse Trendelenburg position, a CPR function status, a center of gravity of a person on the bed frame, a position of the person on the bed frame, and a status of a person-support alarm.

14. The person-support structure of claim 10, wherein the input further comprises a user interface configured to receive a user input, the first input signal including information relating to the user input.

15. The person-support structure of claim 10, wherein the person-support structure includes a person-support surface and the input includes a second sensor coupled to the person-support surface and configured to sense a status of the person-support surface, the first input signal including person-support surface status information.

16. The person-support structure of claim 15, wherein the status of the person-support surface includes at least one of a pressure in a fluid bladder of the person-support surface, a status of a surface therapy, a status of a low-air loss therapy, a status of a percussion vibration therapy, a status of a lateral rotation therapy, a status of an alternating pressure therapy, a status of a surface zone, a status of a surface function, a status of a surface length extension function, a status of a surface length reduction function, a status of a surface width extension function, a status of a surface width reduction function, a status of a turn assist function, a position of a person on the person-support surface, and a morphology of a person on the person-support surface.

17. The person-support structure of claim 10, wherein the first input signal includes information corresponding to the history of a person.

18. The person-support structure of claim 17, wherein the history of the person includes at least one of a preference of a person, a tendency of a person, an electronic medical record (EMR) of a person, a pressure ulcer risk assessment of a person, a medical history of a person, an allergy of a person, a medical condition of a person, a diagnosis of a person, a medication chart for a person, a caregiver assignment history for a person, and a habit of a person.

19. The patient-support structure of claim 10, wherein the control system is configured to communicate with a remote system.

20. The patient-support structure of claim 19, wherein the remote system comprises a nurse call system.

* * * * *